US010391268B2

(12) United States Patent
Zidulka

(10) Patent No.: US 10,391,268 B2
(45) Date of Patent: Aug. 27, 2019

(54) DEVICE AND METHOD OF DELIVERING PARTICLES IN THE UPPER RESPIRATORY TRACT

(71) Applicant: SERVICES MEDICAUX ARNOLD ET JOAN ZIDULKA INC., Côte-Saint-Luc (CA)

(72) Inventor: Arnold Zidulka, Côte Saint-Luc (CA)

(73) Assignee: SERVICES MEDICAUX ARNOLD ET JOAN ZIDULKA INC., Côte Saint-Luc, QC (CA)

( * ) Notice: Subject to any disclaimer, the term of this patent is extended or adjusted under 35 U.S.C. 154(b) by 0 days.

(21) Appl. No.: 15/798,993

(22) Filed: Oct. 31, 2017

(65) Prior Publication Data

US 2018/0043112 A1 Feb. 15, 2018

Related U.S. Application Data

(63) Continuation of application No. PCT/CA2017/050027, filed on Jan. 11, 2017.
(Continued)

(51) Int. Cl.
*A61M 15/00* (2006.01)
*H04L 29/06* (2006.01)
(Continued)

(52) U.S. Cl.
CPC ....... *A61M 15/0086* (2013.01); *A61K 9/0073* (2013.01); *A61K 9/0075* (2013.01);
(Continued)

(58) Field of Classification Search
CPC ............ A61M 15/0086; A61M 15/009; A61M 15/0021
See application file for complete search history.

(56) References Cited

U.S. PATENT DOCUMENTS 1,586,716 A 6/1926 Snow, Jr.
2,788,784 A 4/1957 Birch et al.
(Continued)

FOREIGN PATENT DOCUMENTS

EP 0957961 B1 8/2002
WO WO 01/58514 A1 8/2001

OTHER PUBLICATIONS

Chantal Darquenne et al., Aerosol Deposition in the Human Respiratory Tract Breathing Air and 80:20 Heliox, J Aerosol Med. 2004; 17(3): 278-285.
(Continued)

*Primary Examiner* — Timothy A Stanis
(74) *Attorney, Agent, or Firm* — Anglehart et al.

(57) ABSTRACT

A method of delivering a substance in aerosol or powder form to the upper respiratory tract is provided. The substance is orally administered into the larynx, through the pharynx, and out from the nose while minimizing inhalation into the lungs, whereby deposition of particles in the upper respiratory tract is achieved with limited deposition in the trachea, lower airways and lungs. Also provided is an oral delivery device having a mouthpiece for oral inhalation of a flow of a substance into the upper respiratory tract and a flow restrictor for enabling arrestment of the flow minimizing inhalation into the trachea, lower airways and lungs, which provides for a deposition of particles in the upper respiratory tract with limited deposition in the trachea, lower airways and lungs. Also provided is an oral delivery device having a mouthpiece for admission of a flow of a substance into the upper respiratory tract and a flow generator for pressuring the substance into travel through the upper respiratory tract.

7 Claims, 9 Drawing Sheets

Related U.S. Application Data

(60) Provisional application No. 62/312,878, filed on Mar. 24, 2016.

(51) Int. Cl.

| | |
|---|---|
| *H04L 29/08* | (2006.01) |
| *A61M 16/00* | (2006.01) |
| *A61K 9/00* | (2006.01) |
| *A61K 31/58* | (2006.01) |
| *A61M 16/14* | (2006.01) |
| *G06F 19/00* | (2018.01) |
| *A61M 11/00* | (2006.01) |
| *G16H 20/13* | (2018.01) |

(52) U.S. Cl.
CPC ............ *A61K 9/0078* (2013.01); *A61K 31/58* (2013.01); *A61M 15/0021* (2014.02); *A61M 16/0003* (2014.02); *A61M 16/14* (2013.01); *G06F 19/3456* (2013.01); *H04L 63/1416* (2013.01); *H04L 63/1425* (2013.01); *H04L 63/1433* (2013.01); *H04L 67/02* (2013.01); *A61M 11/007* (2014.02); *A61M 11/008* (2014.02); *A61M 15/002* (2014.02); *A61M 15/009* (2013.01); *A61M 15/0016* (2014.02); *A61M 2202/064* (2013.01); *A61M 2205/581* (2013.01); *A61M 2210/065* (2013.01); *A61M 2210/0618* (2013.01); *A61M 2210/1028* (2013.01); *G16H 20/13* (2018.01)

(56) References Cited

U.S. PATENT DOCUMENTS

| | | | |
|---|---|---|---|
| 4,534,343 A | 8/1985 | Nowacki et al. | |
| 4,790,305 A | 12/1988 | Zoltan et al. | |
| 5,040,527 A | 8/1991 | Larson et al. | |
| 5,042,467 A | 8/1991 | Foley | |
| 5,431,154 A | 7/1995 | Seigel et al. | |
| 5,522,380 A | 6/1996 | Dwork | |
| 5,579,760 A | 12/1996 | Kohler | |
| 5,672,581 A | 9/1997 | Rubsamen et al. | |
| 5,738,087 A | 4/1998 | King | |
| 5,797,392 A | 8/1998 | Keldmann et al. | |
| 5,906,202 A * | 5/1999 | Schuster | A61M 15/0045 128/203.12 |
| 6,039,042 A | 3/2000 | Sladek | |
| 7,013,896 B2 | 3/2006 | Schmidt | |
| 7,900,625 B2 | 3/2011 | Kleinstreuer et al. | |
| 8,251,876 B2 | 8/2012 | Boerst et al. | |
| 8,371,292 B2 * | 2/2013 | Bethke | A61K 9/0075 128/200.24 |
| 8,770,188 B2 | 7/2014 | Stenzler et al. | |
| 8,894,604 B2 | 11/2014 | Vecellio-None et al. | |
| 2003/0168057 A1 * | 9/2003 | Snyder | A61M 15/0065 128/200.21 |
| 2003/0205229 A1 | 11/2003 | Crockford et al. | |
| 2008/0066741 A1 | 3/2008 | LeMahieu et al. | |
| 2013/0092162 A1 | 4/2013 | Kunimoto | |
| 2013/0327323 A1 * | 12/2013 | Rubin | A61M 11/02 128/200.18 |

OTHER PUBLICATIONS

David K. DuBay et al., Aerodynamic Particle Size Analysis of First Defense Pepper Spray, 2003 Specification maual.

David L. Swift, Aerosol deposition and clearance in the human upper airways. Annals of Biomedical Engineering, Sep. 1981, vol. 9, Issue 5, pp. 593-604.

David Swift, Regional aerosol deposition in human upper airways, Nov. 1997, Johns Hopkins Univ.

PCT/CA2017/050027 international search report.
PCT/CA2017/050027 written opinion.
PCT/CA2017/050027 IPRP with related claims.

* cited by examiner

DEVICE AND METHOD OF DELIVERING PARTICLES IN THE UPPER RESPIRATORY TRACT

This application is a continuation application of PCT application PCT/CA2017/050027 filed on Jan. 11, 2017, which claims priority of U.S. provisional application 62/312,878 filed on Mar. 24, 2016.

TECHNICAL FIELD

The invention relates to the medical industry, and more specifically, to the delivery of particles in the respiratory tract.

BACKGROUND

The upper airway cough syndrome causes chronic cough and pharyngeal secretions. These syndromes are often attributable to post nasal drip and rhinitis, which is an inflammation of the mucosal lining the nasal cavity that may block the nasal airways.

One of the main treatments consists in administering aerosolized corticosteroid through the nasal airways. The patient sprays corticosteroid through the nostrils and inhales in hopes that the flow of corticosteroid particles will travel through the nose, into the oropharynx, and possibly into the larynx to eliminate, or at the very least reduce the symptoms of the upper airway cough syndrome. However, the flow of particles is often arrested in the anterior region of the nasal cavities due to anatomical encumbrances in the form of turbinates, which may be swollen, particularly in patients suffering from rhinitis. This prevents sufficient deposition of particles in the regions producing the aforementioned secretions: the posterior region of the nasal cavity, the pharynx, and the larynx. As a result, the treatment is often of limited effectiveness.

Deposition of particles in the pharynx and larynx can be achieved incidentally through oral inhalation of asthma medication. A corticosteroid or other asthma medication may be packaged in a pressurized canister operably connectable with a mouthpiece. The patient inserts the mouthpiece in the mouth, depresses the canister, which releases the corticosteroid in aerosolized form, and inhales the released corticosteroid from the mouthpiece, through the oral and laryngeal cavities, and into the lungs. The majority of the corticosteroid is deposited on the airways of the lungs, causing limited reflux on the following exhalation.

SUMMARY

It is an object of the present invention to provide a method for effective deposition of particles in the oral, laryngeal, pharyngeal, and nasal cavities with limited deposition in the trachea, lower airways and lungs. The purpose of the deposition can be for treatment of a disease of the upper airway or simply as a delivery tool of a medicine to the bloodstream.

The Applicant has found that in a method of delivering a dose of a substance in the upper respiratory tract, the step of orally administering the substance in aerosol or powder form into the larynx, through the pharynx, and out from the nose while minimizing inhalation of the substance into the trachea, lower airways and lungs provides the advantage of a deposition of particles of the substance in the oral, laryngeal, pharyngeal, and nasal cavities with limited deposition in the trachea, lower airways and lungs.

In accordance with an embodiment of the present invention, there is provided a method of delivering a dose of a substance in aerosol or powder form to the upper respiratory tract, the method comprising the step of orally administering the substance into the larynx, through the pharynx, and out from the nose while minimizing inhalation of the substance into the lungs whereby deposition of particles of the substance in the oral, laryngeal, pharyngeal, and nasal cavities is achieved with limited deposition of the particles in the trachea, lower airways and lungs.

It is an object of the present invention to provide a method of treating a disease of the upper respiratory tract.

The Applicant has found that in a method of treating a disease of the upper respiratory tract involving administration of a therapeutically effective dose of a medicament in aerosol or powder form into the respiratory tract, the step of administering the dose orally into the larynx, through the pharynx, and out from the nose while minimizing inhalation into the lungs provides the advantage of a deposition of particles of the medicament in the oral, laryngeal, pharyngeal, and nasal cavities with limited deposition in the trachea, lower airways and lungs.

It is an object of the present invention to provide an oral delivery device for effective deposition of particles in the oral, laryngeal, pharyngeal, and nasal cavities with limited deposition in the trachea, lower airways and lungs.

The Applicant has found that in an oral delivery device for delivering a substance in aerosol or powder form to the respiratory tract, the oral delivery device having a mouthpiece adapted to be received in the mouth for oral inhalation of a flow of the substance into the respiratory tract, a flow restrictor for enabling arrestment of the flow before inhalation into the lungs provides the advantage of effective deposition of particles in the oral, laryngeal, pharyngeal, and nasal cavities following nasal exhalation, and this, with limited deposition in the trachea, lower airways and lungs.

In accordance with one aspect of the present invention, there is provided an oral delivery device for delivering a dose of a substance in aerosol or powder form to the upper respiratory tract, the delivery device comprising a mouthpiece adapted to be received in the mouth for oral inhalation of a flow of the substance into the upper respiratory tract; and a flow restrictor for enabling arrestment of the flow before inhalation into the trachea, lower airways and lungs, whereby a nasal exhalation of the flow following the arrestment completes a deposition of particles of the aerosolized substance in the oral, laryngeal, pharyngeal, and nasal cavities with limited deposition of the particles in the trachea, lower airways and lungs.

The Applicant has also found that in an oral delivery device for delivering a dose of a substance in aerosol or powder form to the respiratory tract, the oral delivery device having a mouthpiece adapted to be received in the mouth for oral admission of a flow of the substance into the respiratory tract, a flow generator for pressuring the substance into the flow travelling through the mouthpiece, into the mouth, and out from the nose while inhalation is avoided provides the advantage of effective deposition of particles in the oral, laryngeal, pharyngeal, and nasal cavities following nasal exhalation, and this, with limited deposition in the trachea, lower airways and lungs.

In accordance with one aspect of the present invention, there is provided an oral delivery device for delivering a dose of a substance in aerosol or powder form to the upper respiratory tract, the oral delivery device comprising a mouthpiece adapted to be received in the mouth for admission of a flow of the substance into the upper respiratory tract; and a flow generator for pressuring the substance into the flow travelling through the mouthpiece, into the mouth, and out from the nose while inhalation is avoided, whereby the dose is delivered with limited deposition of the particles in the trachea, lower airways and lungs.

According to yet another embodiment of the invention, there is provided a use of a corticosteroid in the manufacture of a medicament to be orally administered in aerosol or powder form in the oral, laryngeal, pharyngeal, and nasal cavities for the treatment of a disease of the upper respiratory tract.

BRIEF DESCRIPTION OF THE DRAWINGS

The invention will be better understood by way of the following detailed description of embodiments of the invention with reference to the appended drawings, in which.

DETAILED DESCRIPTION

The invention relates to the medical industry, and more specifically, to the delivery of particles to the respiratory tract. It is an object of the present invention to provide a method for effective deposition of particles in the oral, laryngeal, pharyngeal, and nasal cavities with limited deposition in the trachea, lower airways and lungs.

Figure 1:
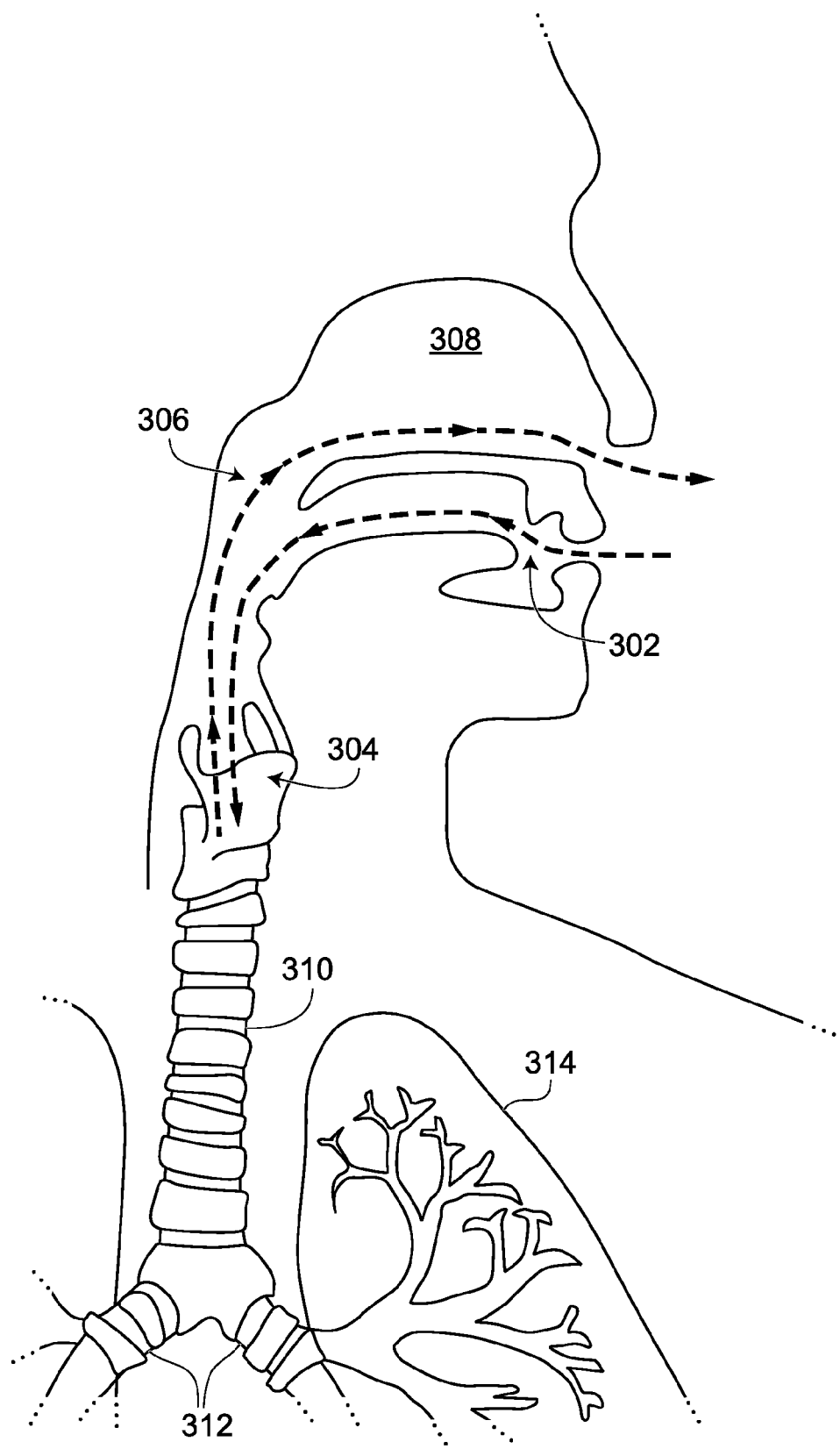
FIG. 1 is a partial saggital view of the respiratory tract where the flow of a substance through the upper respiratory tract is indicated by an arrow.

Referring to FIG. 1, there is shown the respiratory tract. It is sometimes desirable to deliver particles of a substance in the oral cavity 302, the laryngeal cavity 304, the pharyngeal cavity 306, and the nasal cavities 308, whether for the treatment of a medical condition of the upper respiratory tract, such as post-nasal drip or upper airway cough syndrome, to improve the condition of the upper respiratory tract, or for expedited delivery within the blood stream. A nasally inhaled flow of the substance is often arrested in the anterior region of the nasal cavities 308 due to anatomical encumbrances, particularly in a person suffering from rhinitis, which prevents sufficient deposition of particles in the laryngeal cavity 304, the pharyngeal cavity 306, and part of the nasal cavities 308.

The method of the present invention provides for a more effective deposition of particles. In application, the user orally administers the substance in aerosol or powder form into the pharyngeal cavity 306, the laryngeal cavity 304, and possibly the tracheal cavity 310, and out through the pharyngeal cavity 306 and from the nasal cavities 308, as shown by the arrow, while minimizing inhalation into the trachea 310, lower airways 312 and lungs 314. As the administered substance travels through the upper respiratory tract without any anatomical hindrances such as those found in the nasal cavities 308, particles are deposited along the way onto the inner lining to achieve the desired effect. It is important to note that in applying the method, the user minimizes any deposition into the lower airways 312 and lungs 314 as such deposition would be needless, could compromise the effectiveness of the method by reducing the number of particles available for deposition in the laryngeal cavity 304, the pharyngeal cavity 306 and the nasal cavities 308, and could be harmful in cases where inhalation into the lower airways and lungs 314 could cause damage.

In some embodiments, once the substance is administered through the oral cavity 302, its progression through the remaining cavities of interest is facilitated by nasal exhalation. More specifically, when the user exhales through the nose, a flow of air departing from the lungs 314 pushes the administered substance through the laryngeal cavity 304, pharyngeal cavity 306, and nasal cavities 308 to complete the deposition of particles therein. Yet in other embodiments, the user inhales to fill up the lungs 314 and subsequently operates a mechanical device to pressure the substance into a flow directed toward the back of the oral cavity 302. Since the lungs are filled up, the flow cannot progress towards the lungs 314. Similarly, since the flow is directed towards the back of the oral cavity 302, no substantial volume of the flow can regress back towards the mouth. As a result, the flow is directed towards the laryngeal cavity 304, pharyngeal cavity 306, and nasal cavities 308 to complete the deposition of particles therein.

In some embodiments, the dose is administered by oral inhalation, which is to be arrested before admission of any substantial quantity of the substance into the trachea, lower airways and lungs 314. During the following nasal exhalation, a flow of air departing from the lungs 314 pushes the inhaled substance through the laryngeal cavity 304, pharyngeal cavity 306, and nasal cavities 308 to complete the deposition of particles therein. Yet in other embodiments, the dose is administered by operating a mechanical means that pressures the substance into a flow directed towards the back of the oral cavity 302. As mentioned previously, prior to operating the mechanical means, the user fills up the lungs 314, thereby preventing admission of the flow therein.

In some embodiments, the substance is sprayed into an antistatic chamber in fluid communication with a mouthpiece. While in the antistatic chamber, the particles of the substance are maintained in suspension until they are drawn from the chamber and into the mouthpiece before entering the oral cavity 302. The particles can be drawn by oral inhalation from the mouthpiece or by operation of a mechanical means that pressures the particles out of the chamber and into the mouthpiece. In other embodiments, the substance is released in powder form, and the particles of the substance are maintained in suspension until they are drawn into the mouthpiece before entering the oral cavity 302. The particles can be drawn by oral inhalation from the mouthpiece or by operation of a mechanical means that pressures the particles out into the mouthpiece.

The operation of the mechanical means can consist in collapsing a chamber, which reduces its capacity, thereby pressuring its content into a flow directed towards the mouthpiece. For exemplary purposes, the chamber can be a bellows collapsible under two opposite forces exerted by the user thereon. Alternatively, the mechanical means can consist in a plunger moveably mounted within a chamber, wherein the user can move the plunger against the chamber's content to produce a flow directed towards a mouthpiece.

In embodiments where the dose is administered by oral inhalation, the user is to inhale a volume greater than a first threshold, which provides for the deposition of particles in the upper respiratory tract, namely the oral cavity 302, the laryngeal cavity 304, the pharyngeal cavity 306, and the nasal cavities 308, yet smaller than a second threshold to minimize deposition into the trachea, lower airways and lungs 314.

In some embodiments, the oral inhalation is to be arrested by the user in a timely manner, which is challenging as the lapse of time between reaching the first and second thresholds is short. The user is likely to mistime arrestment, stopping short of the first threshold for fear of inhaling into the trachea, lower airways and lungs 314, or staying the course after the second threshold has been reached, for fear of inhaling an insufficient dose. For this reason, in some embodiments, the rate at which the aerosolized substance is inhaled is restricted so as to extend the lapse of time between reaching the first and second thresholds and enable the user to arrest inhalation in a timely manner. For instance, in embodiments where the substance is inhaled from a chamber through a mouthpiece, the outlet through which the chamber communicates with the mouthpiece can be sized so as to sufficiently reduce the flow rate. Alternatively, a sensor mounted in the mouthpiece or chamber can measure the volume moved from the chamber and into the mouthpiece, and emit a signal indicating to the user that oral inhalation is to be arrested. In yet another embodiment, the chamber is a bag that gradually collapses as its content is orally inhaled, the bag being configured to reach a recognizable state of collapse when oral inhalation is to be arrested.

In other embodiments, the inhalation is to be arrested automatically, without any intervention on the part of the user. For instance, in embodiments where the substance is orally inhaled from a chamber through a mouthpiece, a sensor mounted in the mouthpiece or chamber can measure the volume moved from the chamber and into the mouthpiece, and emit a signal once the volume reaches the first threshold. A shutter mounted within the chamber or the mouthpiece interrupts the flow in response to the signal, thereby ensuring arrestment of inhalation and minimizing the amount of substance that reaches the trachea, lower airways and lungs 314.

The first and second thresholds may vary according to the user profile. For instance, if the condition to be treated is severe, a greater dose may be preferred, which translates into a greater first threshold. However, if the user is a child, the respiratory tract is shorter, which translates into a smaller second threshold. In some embodiments, the method of the present invention comprises the step of adjusting the sensor according to the user's profile so as to ensure that arrestment is either suggested to the user or automatically performed in a timely manner. In embodiments where the substance is orally inhaled from the chamber through a mouthpiece, the size of the outlet between the chamber and mouthpiece can be variably restricted using an adjustable valve so as to tailor the rate at which the content is inhaled. For instance, if the user is a child with a severe condition, the lapse of time between reaching the first and second thresholds may be shorter than for other users, and therefore, the valve can be adjusted to further restrict the size of the outlet.

The method of the present invention can be used for the treatment of a medical condition of the upper respiratory tract by providing for the delivery of a therapeutically effective dose of a medicament in the oral cavity 302, the laryngeal cavity 304, the pharyngeal cavity 306, and the nasal cavities 308. For instance, it can be used for the treatment of allergic and non-allergic rhinitis, rhinosinusitis, and upper airway cough syndrome by providing for the delivery of a therapeutically effective dose of an aerosolized corticosteroid. In some embodiments, the therapeutically effective dose of an aerosolized corticosteroid for the treatment of allergic and non-allergic rhinitis, rhinosinusitis, and upper airway cough syndrome is from 25 to 1000 micrograms. Alternatively, the method of the present invention can be used for the treatment of a non-medical condition of the upper respiratory tract by providing for the delivery of an effective dose of a substance in the oral cavity 302, the laryngeal cavity 304, the pharyngeal cavity 306, and the nasal cavities 308. Alternatively, the method of the present invention can be used for the treatment of a medical condition by providing for the expedited delivery of a therapeutically effective dose of a medicament into the bloodstream through the lining of the oral cavity 302, the laryngeal cavity 304, the pharyngeal cavity 306, and the nasal cavities 308, and this, even if the condition to be treated fails to affect the upper respiratory tract. For instance, the method can be used to expeditiously deliver a therapeutically effective dose of sumatriptan into the bloodstream for the treatment of migraines.

The Applicant has performed two rounds of testing on a patient suffering from post-nasal drip and upper laryngeal syndrome with an interval of two weeks between the rounds, each round consisting in administering a therapeutically effective dose of ciclesonide using the method of the present invention. Immediately prior to each one of the rounds, the patient reported experiencing symptoms typical of upper airway cough syndrome, yet following each one of the rounds, the patient reported a significant alleviation of the symptoms. In some embodiments, the therapeutically effective dose of ciclesonide for the treatment of upper airway cough syndrome is from 25 to 800 micrograms. Use of ciclesonide for the treatment of upper airway cough syndrome provides the advantage of avoiding fungal infections typically associated with administration of corticosteroid in the posterior nasal region, pharynx and the larynx.

Figure 3:
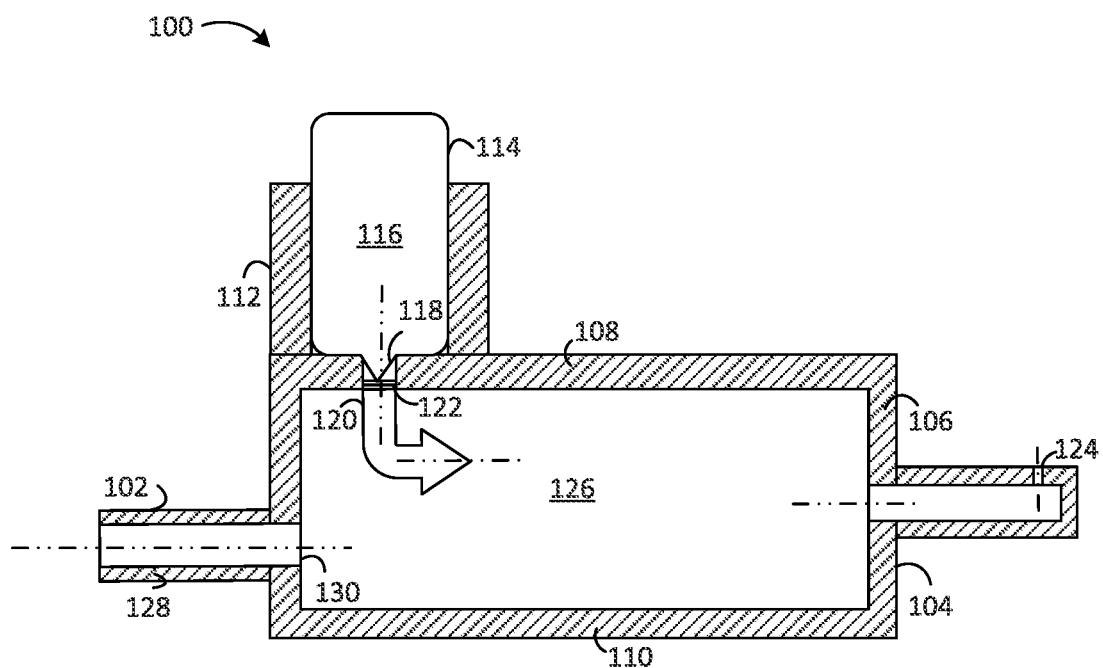
FIG. 3 is a side elevation, cross-section view of a second embodiment of the oral delivery device of the present invention having the chamber in fluid communication with the ambient atmosphere through an opening sized to restrict inhalation rates, the chamber and the mouthpiece being positioned along a longitudinal axis of the device.

In conducting the rounds of testing, the Applicant used the embodiment of the oral delivery device of the present invention shown in FIG. 3. The oral delivery device had an effective volume of 375 milliliters. It should be noted that in some embodiments, the effective volume is greater or smaller than 375 milliliters. In operation, the patient released two sprays of aerosolized ciclesonide into the oral delivery device, each one of the sprays containing 200 micrograms of ciclesonide, and performed four to six oral inhalations, each one of the inhalations being followed by a nasal exhalation into the ambient atmosphere. Each one of the inhalations drew ambient air into the oral delivery device to sweep in an additional amount of aerosolized ciclesonide. On average, the patient admitted 16 milliliters of aerosolized ciclesonide into the oral cavity 302, the pharyngeal cavity 306, the laryngeal cavity 304, the tracheal cavity 310, and the nasal cavities 312. Each one of the inhalations generated a peak negative pressure ranging from minus 34 to minus 65 cm $H_2O$, for an average of minus 50.5 cm $H_2O$. While the patient exhaled, the soft palate of the roof of the mouth closed against the tongue, which prevented oral exhalation. The subsequent mouth negative pressure drew ambient air to replenish the oral delivery device for the subsequent inhalation. The combination of one inhalation and one exhalation was performed at a frequency of approximately 24 times per minute. The series of four to six inhalations and exhalations was performed once in the morning and once in the evening for two weeks. After each series of inhalations and exhalations, the subject rinsed the mouth with water to minimize ciclesonide in the oral cavity.

In some embodiments of the method of the present invention, the delivery of the dose is distributed over several iterations of the previously disclosed step of orally administering the substance, each iteration providing for the delivery of a sub-dose, the sub-dose having been established as a function of the dose to be delivered and the number of iterations.

In some embodiments, the method of the present invention comprises the step of adjusting the number of iterations according to the user's profile. For instance, if the user is a child with a severe condition, the lapse of time between reaching the first and second thresholds may be shorter than for other users. Distribution over several iterations is particularly useful in such cases. When orally administering a sub-dose rather than a dose, the first threshold is reached in a shorter amount of time, thereby extending the lapse of time between reaching the first and second thresholds.

While the method of the present invention has been described as involving minimizing inhalation into the trachea, lower airways and lungs 314, it can alternatively involve minimizing of inhalation into other regions within the respiratory tract, such as the trachea 310 and the primary bronchi 312. Yet in other embodiments, the method can involve inhalation into the trachea 310, but minimizing the amount into the trachea 310, primary bronchi 312 and the lungs 314. Arrestment of the flow, whether performed by the user or by a mechanism such as a shutter operated by a sensor would be adjusted accordingly.

The method of the present invention can be performed using a variety of devices. It is an object of the present invention to provide an oral delivery device for effective deposition of particles in the oral, laryngeal, pharyngeal, and nasal cavities while minimizing deposition into the trachea, lower airways and the lungs.

Figure 2:
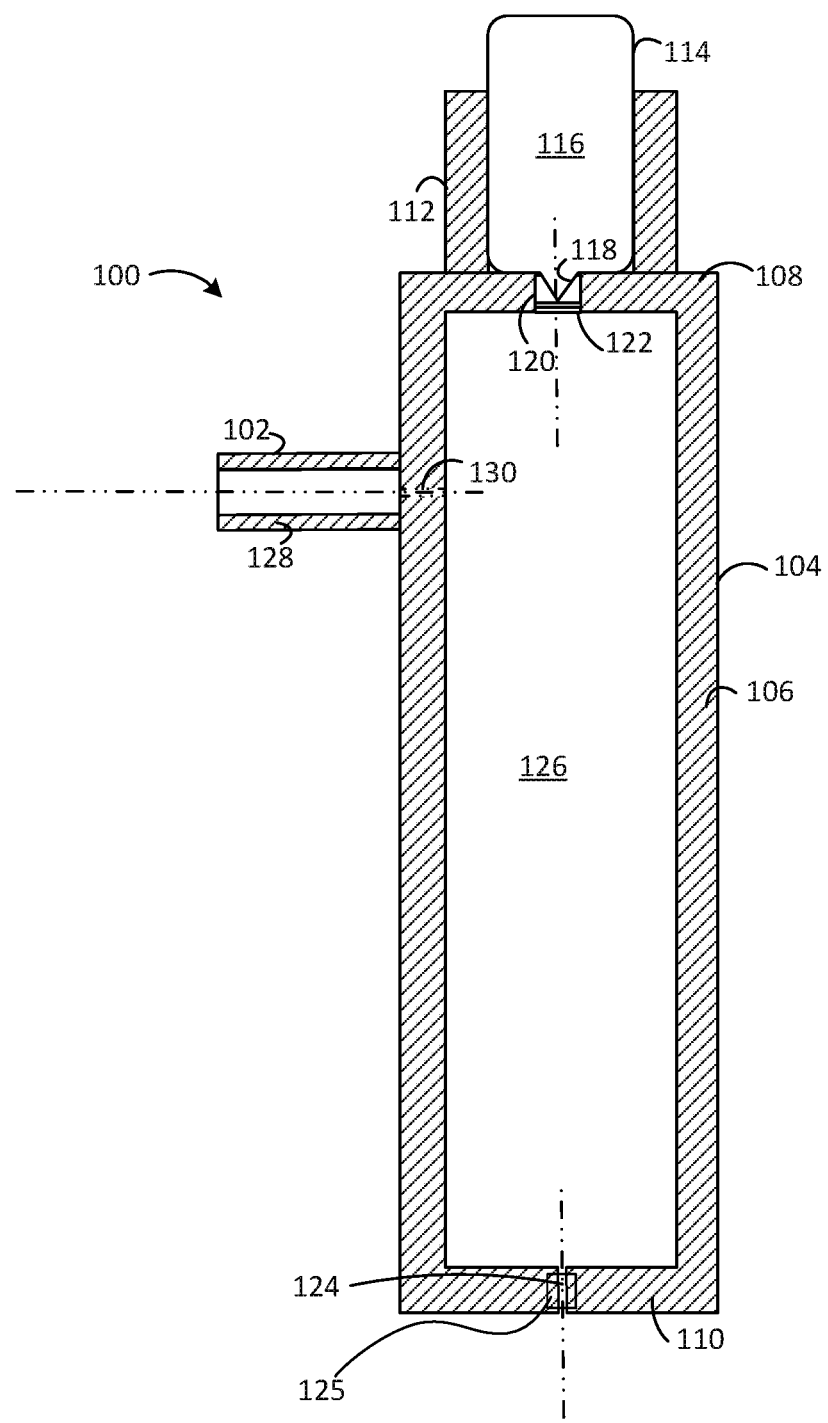
FIG. 2 is a side elevation, cross-section view of a first embodiment of the oral delivery device of the present invention having a chamber in fluid communication with the ambient atmosphere and with a mouthpiece through openings sized to restrict inhalation rates.

Referring now to FIG. 2, there is shown a first embodiment of an oral delivery device 100 having a mouthpiece 102 and a delivery regulator in the form of a flow restrictor.

The flow restrictor has a molded plastic chamber 104, which is hermetically sealed, cylindrical, and of suitable size, weight, and shape to be held in a human hand. The chamber 104 has cylindrical sidewalls 106, a transverse top wall 108, and a transverse bottom wall 110, all of which are preferably made of antistatic material or coated with antistatic material to limit, if not prevent, accumulation of particles thereon. It is important to note that in some embodiments, the cylindrical sidewalls 106, transverse top wall 108, and transverse bottom wall 110, are neither made of nor coated with antistatic material.

Integral with the top wall 108 is a smaller cylindrical wall 112 extending away from the chamber 104 to define an aperture in which a cartridge 114 of pressurized substance 116 is received. The cartridge 114 has a nozzle 118 extending towards the top wall 108 and into a substance inlet 120, which takes the form of a spout extending from the top wall 108 and into the chamber 104, thereby establishing a fluid, one-way communication between the chamber 104 and the cartridge 114. The substance inlet 120 holds a diffuser 122 therein, which is porous and can be made from rigid material such as plastic, or flexible material such as rubber. Upon depression of the cartridge 114 towards the top wall 108, a measured dose of substance 116 is dispensed in aerosolized form within the chamber 104 through the substance inlet 120. Due to the possible antistatic nature of the sidewalls 106, the top wall 108, and the bottom wall 110, more of the dispensed particles of the substance 116 will remain in suspension within the chamber 104 until inhalation from the mouthpiece 102.

The bottom wall 110 defines an air inlet 124 that establishes a fluid one-way communication between the ambient atmosphere and the chamber 104. The air inlet 124 admits air from the ambient atmosphere and into the chamber 104, but limits the release of the content 126 of the chamber 104 into the ambient atmosphere.

Integral with the sidewalls 106 and extending away from the chamber 104 is a cylindrical wall 128 defining a mouthpiece 102. The mouthpiece 102 is of suitable size and shape to be received within the mouth of the user. The sidewalls 106 also define an outlet 130 establishing a fluid, one-way communication between the chamber 104 and the mouthpiece 102. When the user places the mouthpiece 102 in the mouth and inhales, the air inlet 124 admits ambient air into the chamber 104 to produce a flow, and the outlet 130 admits the produced flow from the chamber 104, through the mouthpiece 102, and into the respiratory tract.

The user is to inhale a volume greater than a first threshold, which provides for the deposition of particles in the upper respiratory tract, yet smaller than a second threshold to minimize deposition into the trachea, lower airways and lungs. The oral inhalation is to be arrested by the user in a timely manner, which is challenging as the lapse of time between reaching the first and second thresholds is short. The user is likely to mistime arrestment, stopping short of the first threshold for fear of inhaling into the lungs, or staying the course after the second threshold has been reached, for fear of inhaling an insufficient dose. For this reason, the air inlet 124 and the outlet 130 are sized to restrict the rate at which the aerosolized substance is inhaled is restricted so as to extend the lapse of time between reaching the first and second thresholds and enable the user to arrest inhalation in a timely manner.

In operation, the user places the mouthpiece 102 in the mouth and depresses the cartridge 114 towards the top wall 108, in response to which a measured dose of the substance 116 is dispensed therefrom. The diffuser 122 aerosolizes the dispensed substance 116 before it enters the chamber 104 through the substance inlet 120. Particles of the substance 116 remain suspended in the chamber 104 until the user inhales from the mouthpiece 102, whereupon air is drawn from the ambient atmosphere and into the chamber 104 through the air inlet 124 to mix with the particles of the substance 116. The mixture flows from the chamber 104 and into the mouthpiece 102 through the outlet 130 before entering the oral and laryngeal cavities. The air inlet 124 and the outlet 130 are sized to restrict the rate at which the mixture flows so as to enable the user to arrest inhalation in a timely manner, before the flow is admitted into the trachea, lower airways and lungs. More specifically, as the user inhales, the rate at which the content 126 evacuates the chamber 104 is greater than the rate at which it is replenished. As the chamber 104 is depleted of the content 126, resistance to inhalation increases, leading to a growing discomfort on the part of the user. Upon feeling substantial discomfort, the user arrests inhalation and exhales the flow through the pharynx and out from the nose. As the flow travels through the upper respiratory tract, particles of the substance 116 are deposited in the oral, laryngeal, pharyngeal, and nasal cavities, and this, with minimal deposition within the trachea, lower airways and lungs. While the user exhales, the chamber 104 is replenished with air through the air inlet 124. It is important to note that the oral delivery device 100 enables the user to target areas of the upper respiratory tract that would otherwise be difficult to reach through nasal inhalation due to the anatomical landscape of the nasal cavities. This is achieved while minimizing inhalation of the substance 116 into the trachea, lower airways and lungs, which would result in a waste of the substance 116, if not in damage to the trachea, lower airways and lungs.

The Applicant has found that in an oral delivery device having a mouthpiece adapted to be received in the mouth for oral inhalation of a substance in aerosol or powder form into the upper respiratory tract, a flow restrictor in the form of a chamber in fluid communication with the ambient atmosphere and the mouthpiece through an air inlet and an outlet, at least one of which is sized to restrict the inhalation rates, enables the user to arrest inhalation in a timely manner, thereby providing the advantage of an efficient delivery of particles of the aerosolized substance to the upper respiratory tract, namely the oral, laryngeal, pharyngeal, and nasal cavities with limited deposition in the trachea, lower airways and lungs.

While the air inlet 124 and the outlet 130 have been described as sized to restrict the inhalation rate so as to enable the user to arrest inhalation in a timely manner, in an alternative embodiment, only one of the air inlet 124 and the outlet 130 is sized to achieve such restriction. Also, while the air inlet 124 and outlet 130 have been described as sized to achieve such restriction, they can alternatively benefit from a valve 125 (shown schematically within the inlet 124 in FIG. 2) mounted therein to adjust their size as appropriate. According to yet another embodiment, at least one of the air inlet 124 and outlet 130 benefits from a valve that can be adjusted to tailor the restriction of the inhalation rates according to the user's profile. For instance, since the respiratory tract of a child is not as lengthy as that of an adult, the valve can be adjusted for greater restriction. Also, while the substance inlet 120, the air inlet 124, and the outlet 130 have been described as establishing one-way communications, at least one of them may alternatively establish a two-way communication that does not compromise the effectiveness of the oral delivery device 100.

While the mouthpiece 102 has been described as tubular, it can alternatively take other forms. For instance, the mouthpiece 102 can take the form of a facemask that enables inhalation of the content 126 through the oral airway, but not through the nasal airways. Also, while the oral delivery device 100 has been described as presenting the mouthpiece 102 and the chamber 104 along perpendicular axes, it can alternatively present the mouthpiece 102 and the chamber 104 along a same axis, as shown in FIG. 3.

While the chamber 104 has been described as having the air inlet 124, it can alternatively be devoid of any inlets other than the substance inlet 120. As the user inhales from the mouthpiece 102, the content 126 of the chamber 104 is gradually depleted until a vacuum state is reached, at which point inhalation is arrested. The capacity of the chamber 104 is sufficiently small so that a vacuum state is reached, thereby arresting inhalation before substantial flow reaches the lungs. The capacity is also sufficiently large for the flow to travel through the mouth and larynx during oral inhalation and through the pharynx and nose during nasal exhalation, whereby particles of the aerosolized substance are deposited in the oral, laryngeal, pharyngeal, and nasal cavities as the flow travels through the upper respiratory tract.

While the capacity of the chamber 104 has been described as fixed, it can alternatively be adjustable according to the user's profile prior to use. For instance, since the respiratory tract of children is not as lengthy as that of adults, the capacity of the chamber can be reduced to accommodate children, or conversely expanded to accommodate adults. In one embodiment, and as shown in FIG. 7, the chamber 104 can be a bellows collapsible and expandable to adjust its capacity. Alternatively, in an embodiment shown in FIG. 6, the flow restrictor can have a plunger 136 moveably mounted within the chamber 104 to adjust its capacity.

In some embodiments, the oral delivery device 100 presents a flow restrictor having a chamber 104 in the form of a bag collapsible over the course of inhalation. The bag is made from flexible material such as plastic that shrivels as the flow travels into the mouthpiece 102. In operation, the user places the mouthpiece 102 in the mouth and depresses the cartridge 114, in response to which a measured dose of the substance 116 is dispensed therefrom and processed into an aerosolized form prior to admission into the chamber 104. Particles of the substance 116 dispensed remain suspended in the chamber 104 until the user inhales from the mouthpiece 102, whereupon the content 126 of the chamber 104 flows into the mouthpiece 102 through the outlet 130, before entering the oral and laryngeal cavities. Over the course of inhalation, the chamber 104 collapses towards the mouthpiece 102 until it reaches a state of collapse indicating that the inhalation is to be arrested. A subsequent nasal exhalation completes the deposition of particles of the substance 116 within the oral, laryngeal, pharyngeal, and nasal cavities with limited deposition in the trachea, lower airways and lungs.

Figure 4:
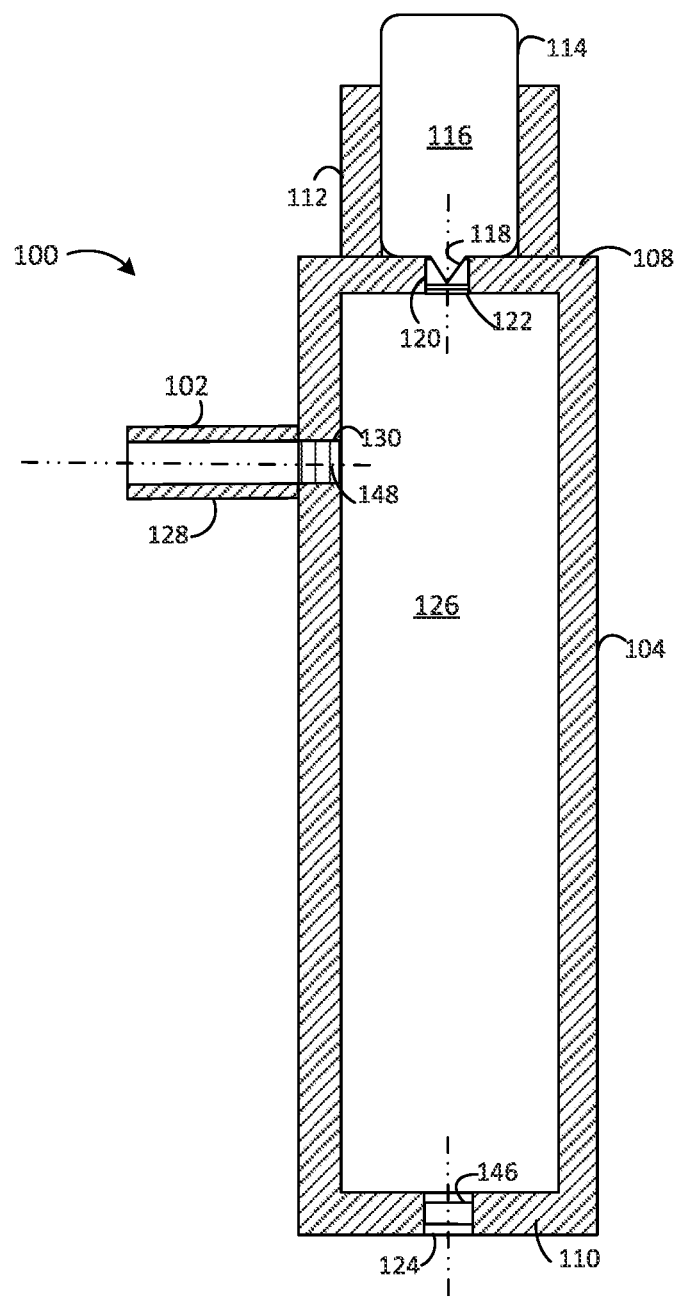
FIG. 4 is a side elevation, cross-section view a third embodiment of the oral delivery device of the present invention having a sensor for emitting a signal upon sufficient inhalation and a shutter for arresting inhalation in response to the signal.
Figure 5:
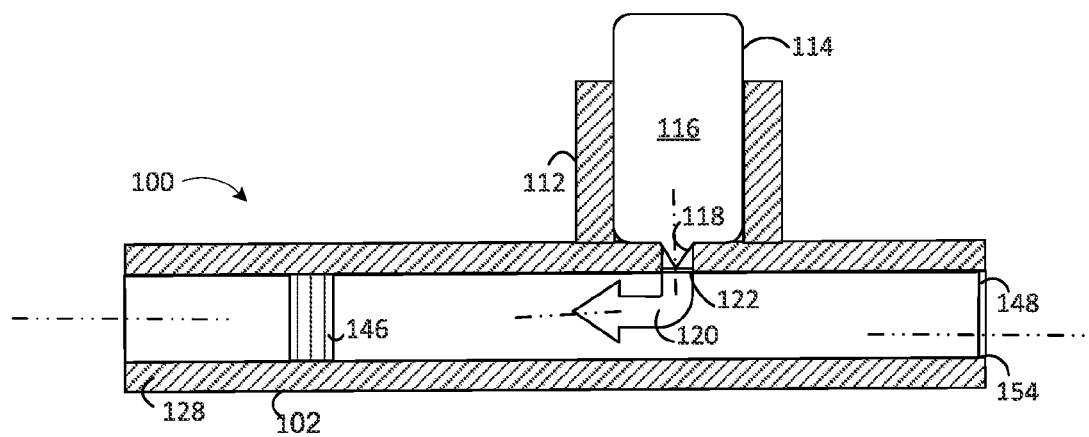
FIG. 5 is a side elevation cross-section view of a fourth embodiment of the oral delivery device of the present invention having a mouthpiece in which the substance is sprayed directly, the device having a sensor for emitting a signal upon sufficient inhalation and a shutter for arresting inhalation in response to the signal.

Referring now to FIG. 4, there is shown a third embodiment of the oral delivery device 100 presenting the mouthpiece 102 and a flow restrictor having the chamber 104, a sensor 146, and a shutter 148. The chamber 104 is in fluid communication with the ambient atmosphere through the air inlet 124 and in fluid communication with the mouthpiece 102 through the outlet 130. When the user inhales from the mouthpiece 102, air is drawn from the ambient atmosphere and into the chamber 104 through the air inlet 124. The sensor 146, mounted within the air inlet 124, measures the volume of air drawn into the chamber 104, which corresponds to the volume of flow drawn from the chamber 104 and into the mouthpiece 102 for oral inhalation. Once the measured volume is sufficiently large for the deposition of particles of the substance 116 in the oral, laryngeal, pharyngeal, and nasal cavities, yet sufficiently small to limit deposition in the trachea, lower airways and lungs, the sensor 146 emits a signal in response to which the shutter 148, mounted in the outlet 130, closes the outlet 130 to arrest inhalation and minimize the flow from reaching the trachea, lower airways and lungs.

In operation, the user places the mouthpiece 102 in the mouth and depresses the cartridge 114 towards the top wall 108, in response to which a measured dose of the substance 116 is dispensed therefrom and aerosolized by the diffuser 122 before being admitted into the chamber 104 through the substance inlet 120. Particles of the substance 116 remain suspended in the chamber 104 until the user inhales from the mouthpiece 102, whereupon air is drawn from the ambient atmosphere and into the chamber 104 through the air inlet 124 to mix with the particles of the substance 116. The mixture flows from the chamber 104 and into the mouthpiece 102 through the outlet 130, before entering the oral and laryngeal cavities. The sensor 146, mounted within the air inlet 124, measures the volume of air drawn into the chamber 104, which corresponds to the volume of the flow drawn out from the chamber 104 and into the mouthpiece 102 for oral inhalation. Once the measured volume is sufficiently large for the deposition of particles of the substance 116 in the oral, laryngeal, pharyngeal, and nasal cavities, yet sufficiently small to limit deposition in the lungs, the sensor 146 emits a signal in response to which the shutter 148, mounted in the outlet 130, closes the outlet 130 to arrest inhalation and minimize the flow from reaching the trachea, lower airways and lungs. The user subsequently exhales the flow through the pharynx and out from the nose. As the flow travels through the upper respiratory tract, particles of the substance 116 are deposited in the oral, laryngeal, pharyngeal, and nasal cavities, and this, with minimal deposition within the trachea, lower airways and lungs.

While the sensor 146 has been described as measuring the air drawn into the chamber 104, it can exclusively conduct such measurements upon depression of the cartridge 114, thereby limiting needless operation of the sensor 146 and shutter 148. Also, in some embodiments, the sensor may be controlled to set the threshold volume that triggers the emission of a signal according to the user's profile. For instance, since the respiratory tract of children is not as lengthy as that of adults, the threshold volume can be decreased accordingly.

While the embodiment shown in FIG. 4 has been described as having the sensor 146 and the shutter 148, it can alternatively be devoid of shutters, in which case the sensor 146 emits a signal perceivable by the user, such as an audio signal, and indicating thereto that the oral inhalation is to be arrested to minimize the flow from reaching the lungs. Also, while the sensor 146 has been described as mounted within the air inlet 124, it can alternatively be mounted elsewhere within the oral delivery device 100, such as within the outlet 130, wherein the sensor 146 measures the volume of content admitted from the chamber 104 and into the mouthpiece 102. While the shutter 148 has been described as mounted in the outlet 130, it can alternatively be mounted elsewhere within the delivery device 100, such as within the mouthpiece 102.

In some embodiments, the delivery device 100 of the present invention can be retrofitted on an asthma inhaler, and presents a mouthpiece in the form of an attachment as well as a flow restrictor. The attachment has a proximal end from which the user can inhale and a distal end, mountable within the mouthpiece 102 of the asthma inhaler by friction fit. The flow restrictor consists in an extension at the distal end of the attachment, the extension defining an opening establishing a fluid communication with the asthma inhaler. The opening is sized to restrict the inhalation rates so as to enable the user to arrest inhalation in a timely manner, namely after having inhaled a volume sufficiently large for the deposition of particles in the upper respiratory tract, yet sufficiently small to minimize deposition in the trachea, lower airways and lungs.

Referring now to FIG. 5, there is shown a fourth embodiment of the oral delivery device 100 presenting a mouthpiece 102 and a flow restrictor. The mouthpiece 102 presents a proximal end for inhaling the content of the mouthpiece 102, and a distal end defining an air opening 154. The flow restrictor presents a sensor 146 and a shutter 148. When the user inhales from the mouthpiece 102, air is drawn from the ambient atmosphere and into the chamber 104 through the air opening 154 to produce a flow. The sensor 146, mounted within the air opening 154, measures the volume of air drawn into the mouthpiece 102, which corresponds to the volume of flow drawn from the mouthpiece 102 and into the upper respiratory tract. Once the measured volume is sufficiently large for the deposition of particles of the substance 116 in the oral, laryngeal, pharyngeal, and nasal cavities, yet sufficiently small to limit deposition in the lungs, the sensor 146, mounted within the air opening 154 emits a signal in response to which the shutter 148, mounted within the mouthpiece 102, closes the mouthpiece 102 to arrest inhalation and minimize the flow from reaching the trachea, lower airways and lungs.

In operation, the user places the mouthpiece 102 in the mouth and depresses the cartridge 114, in response to which a measured dose of the substance 116 is dispensed and aerosolized before it enters the mouthpiece 102. As the particles of the substance 116 enter the mouthpiece 102, the user inhales, drawing air from the ambient atmosphere through the air opening 154 and into the chamber 104 to mix with the particles of the substance 116. The resulting mixture flows into the oral and laryngeal cavities. The sensor 146, mounted within the air opening 154, measures the volume of air drawn into the mouthpiece 102, which corresponds to the volume of mixture inhaled. Once the measured volume is sufficiently large for the deposition of particles of the substance 116 in the oral, laryngeal, pharyngeal, and nasal cavities, yet sufficiently small to limit deposition in the lungs, the sensor 146 emits a signal in response to which the shutter 148, mounted in the mouthpiece 102, closes the mouthpiece 102 to arrest inhalation, thereby preventing any substantial flow from reaching the trachea, lower airways and lungs. The user subsequently exhales the flow through the pharynx and out from the nose. As the flow travels through the upper respiratory tract, particles of the substance 116 are deposited in the oral, laryngeal, pharyngeal, and nasal cavities, and this, with limited deposition within the trachea, lower airways and lungs.

The Applicant has found that in an oral delivery device having a mouthpiece configured to directly receive a substance therein, the mouthpiece having an air opening at a distal end, the air opening being in fluid communication with the ambient atmosphere, the proximal end being adapted to be received in the mouth for oral inhalation of the substance mixed with air drawn from the ambient atmosphere through the air opening, a flow restrictor having a sensor and a shutter, the sensor for measuring the volume inhaled through the mouthpiece and emitting a signal once the measured volume is sufficiently large for deposition of particles in the upper respiratory tract, yet sufficiently small to limit inhalation into the trachea, lower airways and lungs, and the shutter configured to close the mouthpiece, thereby arresting inhalation, in response to the signal emitted by the sensor provides the advantage of an efficient delivery of particles of the aerosolized substance to the upper respiratory tract with limited deposition in the trachea, lower airways and lungs.

While the sensor 146 has been described as measuring the air drawn into the mouthpiece 102, it may exclusively conduct such measurements upon depression of the cartridge 114, thereby limiting needless operation of the sensor 146 and shutter 148. Also, in some embodiments, the sensor 146 may be controlled to set the threshold volume that triggers the emission of a signal according to the user's profile. For instance, since the upper respiratory tract of a child is not as lengthy as that of an adult, the threshold volume can be decreased accordingly.

The previously disclosed oral delivery device of the present invention requires that the user orally inhales a dose of aerosolized substance from a mouthpiece for the dose to be delivered to the upper respiratory tract. Use of such a device can present challenges to users having underdeveloped lungs, such as children, or to users experiencing pulmonary problems hindering their ability to either inhale or exert control over their inhalation. For these reasons, it is desirable to be provided with an alternative device that can be used without performing substantial inhalation, if any.

Figure 6:
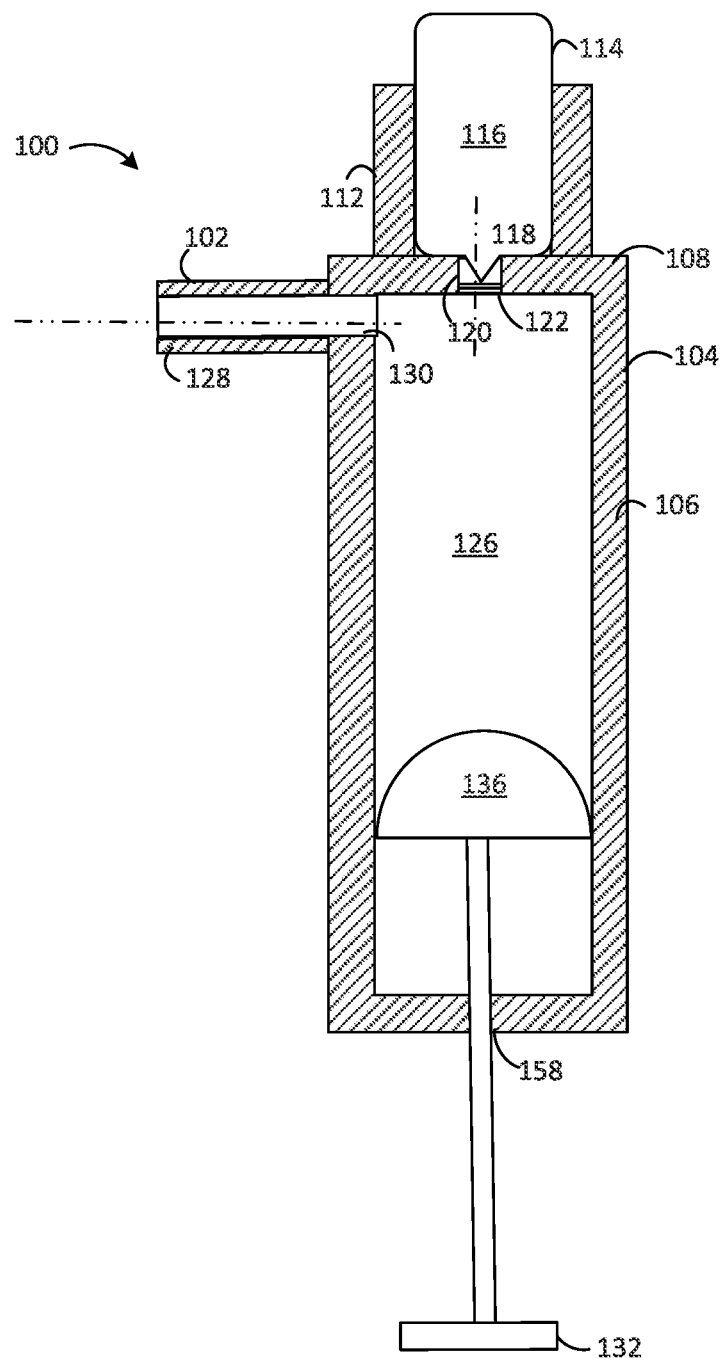
FIG. 6 is a side elevation, cross-section view of a fifth embodiment of an oral delivery device of the present invention, the device having a plunger moveably mounted within a chamber to pressure its content into a flow travelling through the upper respiratory tract.
Figure 7:
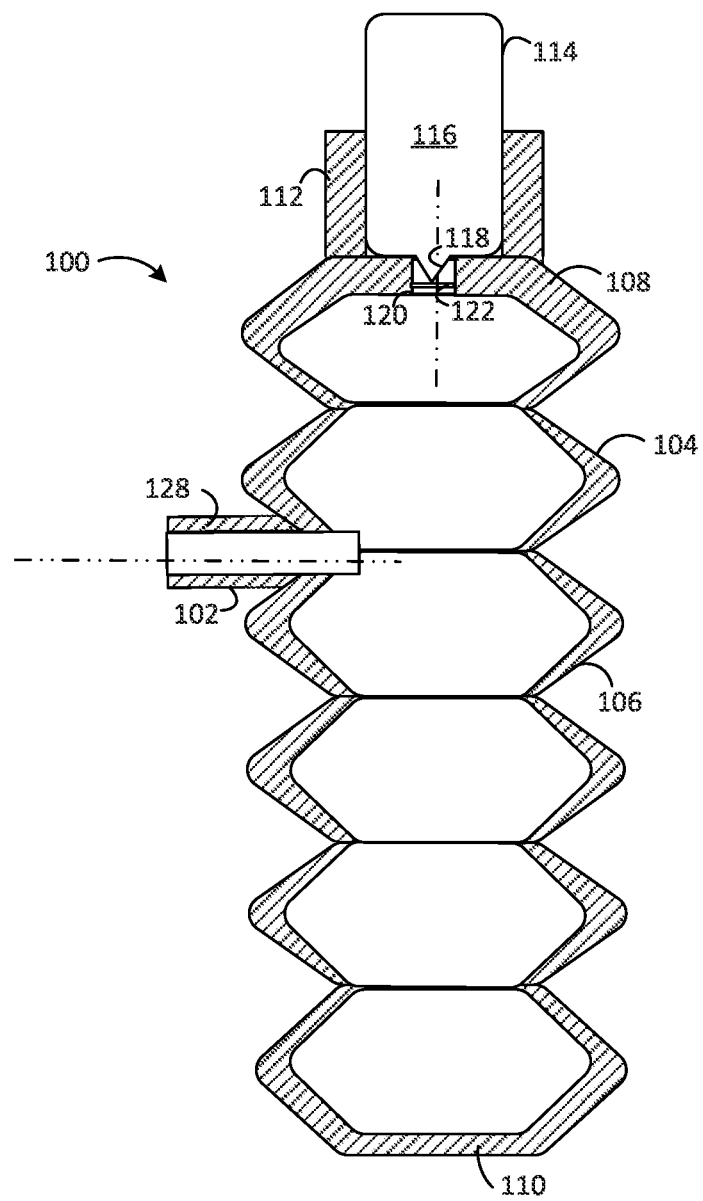
FIG. 7 is a side elevation, cross-section view of a sixth embodiment of the oral delivery device of the present invention having a chamber in the form of a bellows collapsible to pressure its content into a flow travelling through the upper respiratory tract.

Referring now to FIG. 6, there is shown a fifth embodiment of the oral delivery device 100 according to the present invention, the oral delivery device 100 presenting the mouthpiece 102 and a flow generator having the chamber 104 and a plunger 136. The chamber 104 is of capacity to hold a volume which, when administered into the upper respiratory tract, ensures sufficient deposition of particles in the oral, laryngeal, pharyngeal, and nasal cavities. Conversely, the capacity is such that no additional volume can be held beyond that which is necessary, thereby minimizing needless and potentially harmful overexposure to the administered substance. The chamber 104 is in fluid communication with the mouthpiece 102 through an outlet 130 and defines an aperture 158 through which the plunger 136 is moveably mounted. The plunger 136 can be moved against the content 130 of the chamber 104 to pressure the content 126 into a flow travelling through the outlet 130 and into the mouthpiece 102 before entering the upper respiratory tract. The plunger 136 can be moved in the opposite direction to draw in air from the ambient atmosphere through the mouthpiece 102.

The fifth embodiment presents two distinct modes of operation. Under the first mode of operation, the user places the mouthpiece 102 in the mouth and depresses the cartridge 114 towards the top wall 108, in response to which a measured dose of the substance 116 is dispensed and aerosolized by the diffuser 122 before it enters the chamber 104 through the substance inlet 120. Particles of the substance 116 remain suspended in the chamber 104 until the user operates a handle 132 to move the plunger 136 against the content 126 of the chamber 104, thereby pressuring the content 126 into a flow that travels through the outlet 130 and into the mouthpiece 102, before entering into the oral cavity. As the plunger 136 moves along the chamber 104 to a first position, the user inhales sufficiently to admit the portion of the content 126 pressured into the mouthpiece 102, but not enough to admit the remainder of the content 126. The process is repeated until the chamber 104 is depleted of the content 126, at which point the plunger 136 is pulled back towards the bottom wall 110 to replenish the chamber 104 with air. Under this particular mode of operation, the movement of the plunger 136 towards the top wall 108 reduces the volume of the chamber 104 by the volume of the content 126 pressured into the mouthpiece 102. As a result, the portion of the content 126 held in the chamber 104 is at atmospheric pressure and maintains its concentration of aerosolized substance for greater consistency from one inhalation to another.

Alternatively, under the second mode of operation, the user inhales to fill up the lungs, places the mouthpiece 102 in the mouth and depresses the cartridge 114 towards the top wall 108, in response to which a measured dose of the substance 116 is dispensed and aerosolized by the diffuser 122 before it enters the chamber 104 through the substance inlet 120. Particles of the substance 116 remain suspended in the chamber 104 until the user operates a handle 132 to move the plunger 136 against the content 126 of the chamber 104, thereby pressuring the content 126 into a flow that travels through the outlet 130 and into the mouthpiece 102, before entering into the oral cavity. Since the lungs are filled up, the flow would have limited progression towards the trachea, lower airways and lungs. Similarly, since the flow is directed towards the back of the oral cavity, no substantial volume of the flow can regress back towards the mouth. As a result, the flow is directed towards the larynx, the pharynx, and the nose to complete the deposition of particles therein. Once the plunger 136 reaches the upper wall 108, the flow is arrested as the volume administered provides for sufficient deposition of particles in the upper respiratory tract. The user can then return to normal breathing.

The Applicant has found that in an oral delivery device for delivering a dose of a substance in the respiratory tract, the oral delivery device having a mouthpiece adapted to be received in the mouth for oral admission of a flow of the substance into the respiratory tract, a flow generator for pressuring the substance into the flow travelling through the mouthpiece, into the mouth, and out from the nose while inhalation is avoided, and for enabling arrestment of the flow once the flow reaches a volume sufficient for a deposition of particles of the aerosolized substance in the oral, laryngeal, pharyngeal, and nasal cavities provides the advantage of effective deposition of particles in the oral, laryngeal, pharyngeal, and nasal cavities following nasal exhalation, and this, with limited deposition in the trachea, lower airways and lungs.

While it was mentioned that prior to operating the oral delivery device 100, the user inhales to fill up the lungs, thereby preventing the flow from progressing towards the trachea, lower airways and lungs as the substance 116 is administered, the user is not required to hold breath until arrestment of the flow. Alternatively, the user can nasally exhale during administration of the substance, thereby encouraging the flow to progress towards the pharynx and the nose after it reaches the larynx.

While the flow generator has been described as comprising the chamber 104 and the plunger 136, it can alternatively comprise the chamber 104 in the form of a bellows, as shown in FIG. 7, wherein the chamber 104 can be contracted to pressure the content 130 into a flow directed towards the mouthpiece 102, and expanded to draw air from the ambient atmosphere through the mouthpiece 102 and into the chamber 104.

Figure 8:
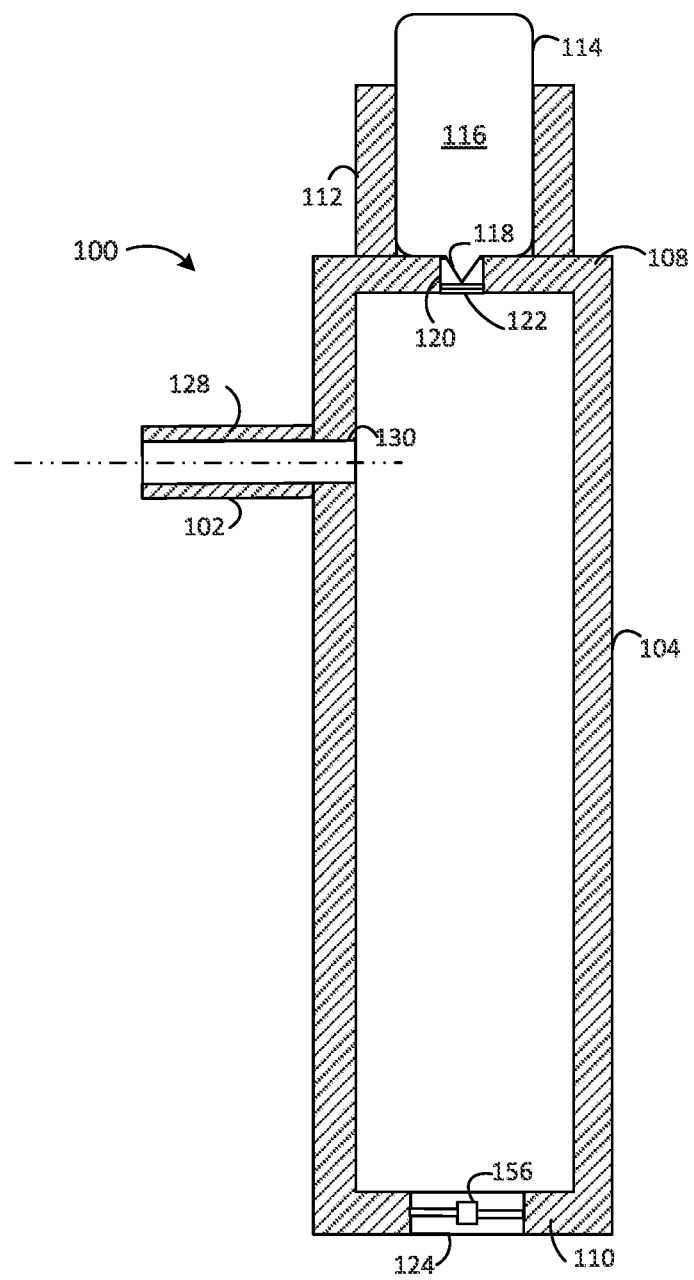
FIG. 8 is a side elevation, cross-section view of a seventh embodiment of the oral delivery device of the present invention, the device having a ventilation element configured to pressure the content of a chamber into a flow travelling through the upper respiratory tract while inhalation is avoided.

Yet in another embodiment, and referring to FIG. 8, the flow generator comprises a ventilation element or fan 156 (for example using battery power) mounted in the air inlet 124 for drawing air from the ambient atmosphere and into the chamber 104 to generate a flow directed towards the mouthpiece 102. The ventilation element 156 can be configured for direct activation by the user, whereby after the aerosolized substance is dispensed within the chamber 104, the user can chose the time at which the administration of the substance is to be initiated. Alternatively, the ventilation element 156 can be configured for activation upon depression of the cartridge 114, whereby fewer steps are required on the part of the user. The ventilation element 156 can be configured to automatically turn off after a specific amount of time, which amount of time is such that the volume administered provides for sufficient deposition of particles in the respiratory tract. In yet another embodiment, a sensor measures the volume drawn into the mouthpiece 102 from the chamber 104 and turns off the ventilation element 156 when the measured volume provides for sufficient deposition of particles in the respiratory tract. In some embodiments, the ventilation element 156 is adjustable according to the user's profile. For instance, the amount of time before the ventilation elements 156 automatically turns off can be reduced if the user is a child.

While the capacity of the chamber 104 has been described as being limited such that no additional volume can be held beyond that which is necessary, it can alternatively hold a greater volume, yet inform the user when a sufficient volume has been administered. For instance, in the embodiment shown in FIG. 6, the sidewalls 106 can bear marked graduations, each of which corresponds to a desired volume for a distinct user profile. Since the respiratory tract of children is not as lengthy as that of adults, the graduation associated with children can be closer to the bottom wall 110, whereas the graduation associated with adults can be closer to the top wall 108. In operation, the plunger 136 is to be arrested at the marking associated with the user's profile. Similar graduations can be marked on the embodiment shown in FIG. 7, wherein the chamber 104 is to be collapsed until it reaches the graduation associated with the user's profile. Alternatively, the chamber 104 can be sized such that a recognizable state of collapse is achieved when the administration is to be arrested. For instance, the chamber 104 can be sized such that once it collapses in half, the administration is to be arrested. In yet another embodiment, a sensor mounted in the oral delivery device 100 measures the volume drawn into the mouthpiece 102 from the chamber 104 and emits a signal perceivable by the user when the measured volume provides for sufficient deposition of particles in the upper respiratory tract, the signal informing the user that the flow is to be arrested. Alternatively, the emitted signal can activate a shutter mounted within the oral delivery device 100 to arrest the flow. The shutter can arrest the flow by, for instance, closing the outlet 130.

Figure 9:
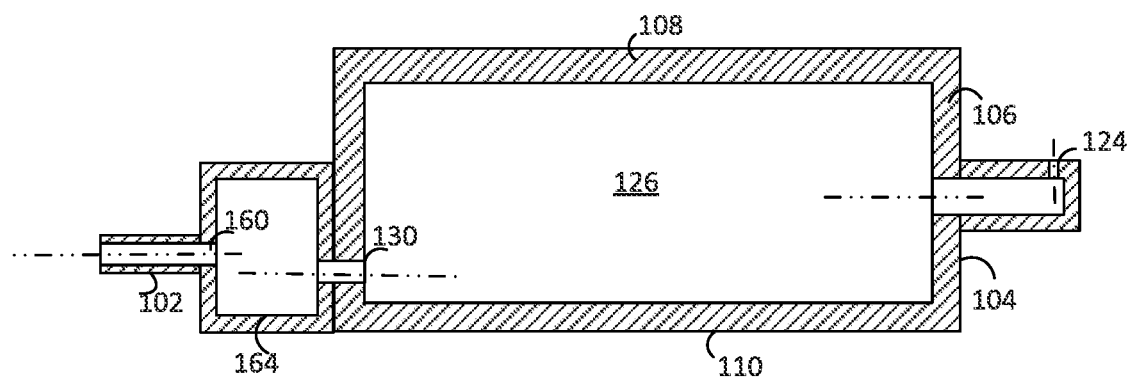
FIG. 9 is a side-elevation, cross-section view of an eighth embodiment of the oral delivery device of the present invention, the device incorporating a powder delivery inhaler.

While the oral delivery device of the present invention has been described as delivering substances in aerosol form, it can alternatively be used to deliver substances in powder form. The embodiments shown in FIG. 2 to FIG. 8 can be adapted for delivery of powder substance to that end. Referring now to FIG. 9, there is shown an eighth embodiment of the oral delivery device 100 presenting the mouthpiece 102, a powder inhalation device 164, and a flow restrictor having the chamber 104. The chamber 104 is in fluid communication with the ambient atmosphere through the air inlet 124, and with the powder inhalation device 164 through the outlet 130. As for the power inhalation device 164, it is also in fluid communication with the mouthpiece 102 through powder inhalation device outlet 160. The content 126 consists of air.

When the user inhales from the mouthpiece 102, the content 126 flows from the chamber 104 and to the powder inhalation device 164 through the outlet 130 for mixing with the powder substance to be delivered. The produces mixture flows through the powder inhalation device outlet 160 and into the mouthpiece 102 for oral inhalation. The air inlet 124 is sized to restrict the rate at which the mixture is inhaled so as to extend the lapse of time between reaching the first and second thresholds and enable the user to arrest inhalation in a timely manner.

In operation, the user places the mouthpiece 102 in the mouth and actuates the powder inhalation device 164, in response to which a measured dose of the powder substance is released in suspension therein. Particles of the powder substance remain suspended in the powder inhalation device 164 until the user inhales from the mouthpiece 102, whereupon air is drawn from the ambient atmosphere and into the chamber 104 through the air inlet 124. The content 126 of the chamber 104, which consists of air, flows from the chamber 104 and into the powder inhalation device 164 through the outlet 130 for mixing with the powder substance. The air inlet 124 is sized to restrict the rate at which the mixture flows so as to enable the user to arrest inhalation in a timely manner, before any substantial flow is admitted into the lungs. More specifically, as the user inhales, the rate at which the content 126 evacuates the chamber 104 is greater than the rate at which it is replenished. As the chamber 104 is depleted of the content 126, resistance to inhalation increases, and this, until the user feels a substantial discomfort, which signals that inhalation is to be arrested. The user subsequently exhales the flow through the pharynx and out from the nose. As the flow travels through the upper respiratory tract, particles of the powder substance are deposited in the oral, laryngeal, pharyngeal, and nasal cavities, and this, with limited, if any, deposition within the trachea, lower airways and lungs. It is important to note that the oral delivery device 100 enables the user to target areas of the upper respiratory tract that would otherwise be difficult to reach through nasal inhalation due to the anatomical landscape of the nasal cavities. This is achieved while minimizing inhalation of the powder substance into the trachea, lower airways and lungs, which would result in a waste of the powder substance at best, if not in damages to the lungs.

What is claimed is:

1. An oral delivery device for use by a user for delivering a dose of a substance in aerosol or powder form to the upper respiratory tract of the user, said oral delivery device comprising:
   a mouthpiece adapted to be received in the mouth of the user for oral admission of a flow of air into the upper respiratory tract of the user;
   a substance inlet for admitting said substance so that said flow of air is configured to carry said substance; and
   a delivery regulator comprising a flow restrictor for enabling arrestment of oral inhalation before admission by inhalation into the lungs of the user of said substance, whereby nasal exhalation of said flow of air following said arrestment completes a deposition of particles of said substance in the oral, laryngeal, pharyngeal, and nasal cavities of the user with limited deposition of said particles in the trachea, lower airways and lungs of the user, said flow restrictor comprising a chamber in fluid communication with said mouthpiece having a volume effective to allow said flow of air into said mouth and an air inlet for admitting ambient air at a restricted rate upon said inhalation from said mouthpiece that is configured to cause the user to feel discomfort, arrest inhalation effort and to exhale out from the nose, the size of the air inlet being fixed for a duration of said delivering said dose, and said air inlet being dimensioned so that user inhalation produces a negative pressure in said chamber below −34 cm of water.

2. The oral delivery device of claim 1, wherein said substance is in aerosol form.

3. The oral delivery device of claim 1, wherein said air inlet is sized to restrict the rate of said inhalation so as to enable a person to whom said dose is delivered to arrest said oral inhalation in a timely manner.

4. The oral delivery device of claim 1, wherein said oral delivery device is adapted for retrofitting on an aerosol or powder medication delivery device.

5. In combination, the oral delivery device of claim 1 and a cartridge containing a corticosteroid and configured to deliver a dose of said corticosteroid, said dose of said corticosteroid is a therapeutically effective dose for the treatment of a medical condition selected from the group consisting of an allergic rhinitis, a non-allergic rhinitis, a rhinosinusitis, and an upper airway cough syndrome.

6. The combination of claim 5, wherein said corticosteroid is ciclesonide.

7. A device for delivering a dose of a substance to the upper respiratory tract of a user, said delivery device comprising:
a mouthpiece;
a substance inlet for admitting said substance; and
a delivery regulator comprising a flow restrictor for enabling arrestment of oral inhalation before admission by inhalation into the lungs of the user of said substance, whereby nasal exhalation of a flow following said arrestment completes a deposition of said substance in the oral, laryngeal, pharyngeal, and nasal cavities of the user with limited deposition of said substance in the trachea, lower airways and lungs of the user, said flow restrictor comprising a chamber in fluid communication with said mouthpiece having a volume effective to allow said flow into said mouth and an air inlet for admitting ambient air at a restricted rate upon said inhalation from said mouthpiece that is configured to cause the user to feel discomfort, arrest inhalation effort and to exhale out from the nose, the size of the air inlet being fixed for a duration of said delivering said dose, and said air inlet being dimensioned so that user inhalation produces a negative pressure in said chamber below −34 cm of water.

* * * * *

UNITED STATES PATENT AND TRADEMARK OFFICE
CERTIFICATE OF CORRECTION

PATENT NO. : 10,391,268 B2  
APPLICATION NO. : 15/798993  
DATED : August 27, 2019  
INVENTOR(S) : Arnold Zidulka It is certified that error appears in the above-identified patent and that said Letters Patent is hereby corrected as shown below:

In the Specification

1. In Column 3, Line 18, delete "saggital" and insert -- sagittal --, therefor.

2. In Column 5, Line 18, after 'consists', delete "in" and insert -- of --, therefor.

3. In Column 5, Line 24, after 'consists', delete "in" and insert -- of --, therefor.

4. In Column 7, Line 17, after 'nasal cavities', delete "312" and insert -- 308 --, therefor.

5. In Column 7, Line 27, after 'exhalations', delete "was" and insert -- were --, therefor.

6. In Column 9, Line 55, before 'inlet 124', insert -- air --, therefor.

7. In Column 12, Line 4, after 'consists', delete "in" and insert -- of --, therefor.

8. In Column 13, Line 45, before '130', delete "content" and insert -- outlet --, therefor.

9. In Column 14, Line 61, after 'content', delete "130" and insert -- 126 --, therefor.

10. In Column 15, Line 64, delete "power" and insert -- powder --, therefor.

Signed and Sealed this  
Twenty-fifth Day of May, 2021

Drew Hirshfeld  
*Performing the Functions and Duties of the*  
*Under Secretary of Commerce for Intellectual Property and*  
*Director of the United States Patent and Trademark Office*